US006274791B1

(12) United States Patent
Dhir et al.

(10) Patent No.: US 6,274,791 B1
(45) Date of Patent: Aug. 14, 2001

(54) **METHODS FOR STRAWBERRY TRANSFORMATION USING *AGROBACTERIUM TUMEFACIENS***

(75) Inventors: Seema Dhir, Warner Robins, GA (US); Maud A. W. Hinchee, Ballwin; Jeanne G Layton, Chesterfield, both of MO (US); Janette V. Oakes, Davis, CA (US)

(73) Assignee: (VPP Corporation) DNA Plant Technology Corporation, Oakland, CA (US)

( * ) Notice: Subject to any disclaimer, the term of this patent is extended or adjusted under 35 U.S.C. 154(b) by 0 days.

(21) Appl. No.: 09/232,085

(22) Filed: Jan. 15, 1999

Related U.S. Application Data

(60) Provisional application No. 60/071,773, filed on Jan. 19, 1998.

(51) Int. Cl.$^7$ .............................. C12N 15/09; C12N 5/10; A01H 5/00
(52) U.S. Cl. ..................... 800/294; 800/278; 435/468; 435/419; 435/430
(58) Field of Search ..................................... 800/278, 294, 800/298; 435/410, 420, 430, 468, 69.1, 419

(56) References Cited

U.S. PATENT DOCUMENTS 5,750,870 * 5/1998 Mathews et al. ..................... 800/205
6,043,410 * 3/2000 Wilkinson ............................ 800/287

OTHER PUBLICATIONS

Dodds et al. Experiments in Plant Culture, Cambridge University Press, 1995.*
Finstad et al. Acta Horticulturae, vol. 385, pp. 86–90, 1995.*
Martinelli et al. Acta Horticulturae, vol. 439, pp. 169–173.*
Horsch, R.B. et al. (1985) "A Simple and General Method for Transferring Genes into Plants" Science, 227:1229–1231.

Nehra, N.S. et al. (1989) "Direct Schoot Regeneration from Strawberry Leaf Disks" J. Amer. Soc. Hort. Sci., 114:1014–1018.
Nehra, N.S. et al. (1990) "Agrobacterium–mediated transformation of strawberry calli and recovery of transgenic plants" Plant Cell. Rep., 9:10–13.
Nehra, N.S. et al. (1990) "Genetic transformation of strawberry by *Agrobacterium tumefaciens* using a leaf disk regeneration system" Plant Cell. Rep., 9: 293–298.
Nyman, M. and Wallin, A. (1992) "Transient gene expression in strawberry (*Fragaria x ananassa* Duch.) protoplasts and the recovery of transgenic plants" Plant Cell Rep., 11:105–108.
James, D.J. et al. "Agrobacterium–Mediated Transformation of the Cultivated Strawberry (*Fragaria x Anannassa* Duch.) Using Disarmed Binary Vectors.." *Plant Science* 69:79–97 (1990).
Mathews, H. et al. "Genetic Trasformation of Strawberry: Stable Integration of a Gene to Control Biosynthesis of Ethylene." *In Vitro Cell. Dev. Biol.* 31:36–43 (1995).
James, D.J. et al. "Agrobacterium–Mediated Transformation of Apple and Strawberry Using Disarmed Ti–Binary Vectors" *Acta Horticulturae,* In Vitro Culture, 280:495–502 (1990).
Rugini, E. and Orlando, R. "High Efficiency Shoot Regeneration from Calluses of Strawberry (*Fragaria x ananassa* Duch.) Stipules of In Vitro Shoot Cultures." *Journal of Horticultural Science* 67:577–582 (1992).
James, D.J. et al. "Transgenic Apples and Strawberries: Advances in Transformation, Introduction of Genes for Insect Resistancel and Field Studies of Tissue Cultured Plants." *Acta Horticulturae,* In Vitro Culture, 336:179–184 (1993).

* cited by examiner

*Primary Examiner*—Gary Benzion
*Assistant Examiner*—Melissa L. Kimball
(74) *Attorney, Agent, or Firm*—Townsend & Townsend & Crew LLP

(57) ABSTRACT

Methods for Agrobacterium-mediated transformation and regeneration of strawberry plants are disclosed. Substitution of glucose or fructose for sucrose in various media preparations results in improved transformation efficiencies.

20 Claims, No Drawings

METHODS FOR STRAWBERRY TRANSFORMATION USING *AGROBACTERIUM TUMEFACIENS*

This application claims the benefit of U.S. Provisional Application No. 60/071,773, filed Jan. 19, 1998.

FIELD OF THE INVENTION

The invention relates to methods of genetically transforming plants and more specifically to genetically transforming strawberry plants. In particular, *Agrobacterium tumefaciens* is used in two protocols to improve transformation efficiencies.

BACKGROUND OF THE INVENTION

Strawberries (*Fragaria X ananassa*) are an important component of the U.S. specialty fruit crop. The fruit is grown in nearly every state, both commercially and in home gardens. The U.S. market value for strawberries was approximately $519 million in 1995, with a value of between $10,000 and $13,000 per acre harvested. Worldwide production is estimated at 2.4 million tons.

Strawberries are prone to multiple diseases including viruses, rots, leaf spots, and root and crown disease. Strawberry viruses are spread by aphids, nematodes, leafhoppers, and pollen. Viruses may also be transmitted from mother plants during planting. Pre- and post-harvest rotting of strawberries reduces yields by up to 15% annually. Gray mold caused by *Botrytis cinerea* is responsible for the majority of losses due to rot. Common leaf spot and leaf scorch reduce the vigor of infected leaves, lowering the robustness, yield, and quality of the fruit. Parasitic nematodes, bacteria, and fungi act to cause root and crown disease, lowering the yield of the crop.

In addition to traditional breeding techniques, incorporation of disease resistance, improvements to flavor and color, increased or modified sugar content, and other desirable traits can be envisioned using the modem tools of molecular biology.

Matthews, H. V. et al. (*In Vitro Cell. Dev. Biol.* 31: 36–43 (1995) and WO 95/35388, Dec. 28, 1995) describe the transformation of strawberries using *Agrobacterium tumefaciens* containing a binary vector. Explants of leaf, meristem, and petiole were co-cultured with Agrobacterium for 1–3 days, followed by an stepwise selection process in media containing 3% sucrose and increasing concentrations of kanamycin. All experimental plant cultures and tissues were maintained in a 16:8 light: dark photoperiod. Strawberry plants were regenerated from pure transgenic explants.

Nehra, N. S. et al. (*J. Amer. Soc. Hort. Sci.* 114: 1014–1018 (1989)) reported shoot regeneration from strawberry leaf disks. Efficient regeneration of Redcoat strawberries was achieved in media containing sucrose, benzyladenine, and indoleacetic acid. Low light intensities were found to be conducive to explant regeneration.

Nehra, N. S. et al. (*Plant Cell Rep.* 9: 10–13 (1990)) describe the transformation of strawberry via callus culture with *Agrobacterium tumefaciens* as the DNA delivery agent. Leaf explants were inoculated with bacterial suspension, and co-cultured on callus induction media containing 3% sucrose. Selection was performed for four weeks on media containing kanamycin, carbenicillin, and cefotaxime. Shoots were regenerated from selected calli, and rooted on medium containing kanamycin, benzyladenine, and indolebutyric acid.

James, D. J. and Barbara, D. J. (*Acta Horticulturae* 280: 495–502 (1990)) describe the transformation of apple and strawberry leaf disks and petioles. The method of Horsch, R. B. et al. (*Science* 227: 1229–1231 (1989), for tobacco and petunia) was used, varying the co-cultivation period, the type and quality of agar, plant growth regulators, and the length of the kanamycin selection step. All media used sucrose as a carbohydrate source.

James, D. J. et al. (*Plant Science* 69: 79–94 (1990)) describe low efficiency transformation of strawberry leaf disks with *Agrobacterium tumefaciens*. Plants were regenerated on MS medium supplemented with benzylaminopurine and 2,4-dichlorophenoxyacetic acid. Cefotaxime and kanamycin were used as selection agents, and sucrose was used as the carbohydrate source.

Nehra, N. S. et al. (*Plant Cell Rep.* 9: 293–298 (1990)) describes the transformation of strawberry via a leaf disk regeneration system. Leaf disks were inoculated with a non-oncogenic *Agrobacterium tumefaciens* strain harboring a binary vector plasmid. Disks were pre-cultured for 10 days on non-selective shoot regeneration medium containing 3% sucrose, and transferred to selective medium containing kanamycin. Selected shoots were multiplied on selective shoot proliferation media. Shoots were rooted and regenerated into strawberry plants.

Nyman, M. and Wallin, A. (*Plant Cell Rep.* 11: 105–108 (1992)) presented transient gene expression in strawberry protoplasts via electroporation. Purified protoplasts were suspended in an electroporation buffer containing 10 mM MES, 1 mM calcium chloride, and 0.5 M glucose as an osmotic support.

There exists a need for improved strawberry transformation methods to promote the engineering of desirable traits into this agronomically important crop.

SUMMARY OF THE INVENTION

The present invention relates to methods of preparing transgenic strawberry plants. The substitution of glucose or fructose for sucrose was found to have a pronounced positive effect on transformation efficiencies. The use of folded, immature leaves, and thidiazuron were also found to be beneficial for the preparation of transgenic strawberry explants, shoots, and plants.

In a preferred embodiment, the invention describes a method for the preparation of transgenic strawberry explants comprising contacting strawberry explants with *Agrobacterium tumefaciens* in a co-cultivation medium containing glucose or fructose.

The *Agrobacterium tumefaciens* may generally contain a nucleic acid sequence endogenous to *Agrobacterium tumefaciens*, a nucleic acid sequence endogenous to strawberry, or a nucleic acid sequence from another organism. Alternatively, the *Agrobacterium tumefaciens* contains a nucleic acid sequence exogenous to strawberry, exogenous to *Agrobacterium tumefaciens*, or exogenous to both strawberry and *Agrobacterium tumefaciens*. The nucleic acid sequence may comprise a selectable marker. The selectable marker may generally be any selectable marker suitable for use in *Agrobacterium tumefaciens* or strawberry, and preferably is NPT II, HPT, or EPSPS.

The method may further comprise an incubation step for incubating the transformed strawberry explants for a delay period in delay media under low light conditions. The light conditions are generally any light conditions suitable for the transformation of strawberries, preferably are between about 0 $\mu$Einsteins $m^{-2}$ $sec^{-3}$ and about 40 $\mu$Einsteins $m^{-2}$ $sec^{-1}$, and more preferably are between about 0 $\mu$Einsteins m$^{-2}$ sec$^{-1}$ and about 20 $\mu$Einsteins m$^{-2}$ sec$^{-1}$. The delay period may be about 0 to about 5 days, preferably about 1 to about 4 days, and more preferably is about 3 days.

The delay medium preferably contains glucose. The glucose concentration may generally be about 0.1% (w/v) to about 20% (w/v), preferably about 1% (w/v) to about 4% (w/v), and more preferably about 2% (w/v) to about 3% (w/v). The explants may generally be prepared from any strawberry tissue, and preferably is prepared from either micropropagated strawberry cultures or strawberry sheath leaves. The sheath leaves are preferably runner leaves, node leaves, or crown leaves. The strawberry sheath leaves are preferably folded leaves.

The co-cultivation medium preferably contains glucose. The glucose concentration may generally be about 0.1% (w/v) to about 20% (w/v), preferably about 1% (w/v) to about 4% (w/v), and more preferably about 2% (w/v) to about 3% (w/v). The co-cultivation medium preferably contains thidiazuron. The concentration of thidiazuron may generally be about 0 $\mu$M to about 20 $\mu$M.

In an alternative embodiment, the invention describes a method for the preparation of transgenic strawberry shoots comprising culturing transformed strawberry explants in selection medium containing glucose or fructose. The selection medium may contain an auxin, a cytokinin, an antibiotic, or a plant selection agent.

The selection medium preferably contains glucose. The glucose concentration may generally be about 0.1% (w/v) to about 20% (w/v), preferably about 1% (w/v) to about 4% (w/v), and more preferably about 2% (w/v) to about 3% (w/v). The selection medium preferably contains thidiazuron. The concentration of thidiazuron may generally be about 0 $\mu$M to about 20 $\mu$M.

The invention further encompasses a method for the preparation of transgenic strawberry plants comprising culturing transformed strawberry shoots in rooting medium containing glucose or fructose. The rooting medium preferably contains glucose. The glucose concentration may generally be about 0.1% (w/v) to about 20% (w/v), preferably about 1% (w/v) to about 4% (w/v), and more preferably about 2% (w/v) to about 3% (w/v). Alternatively, the rooting medium contains fructose. The fructose concentration may generally be about 0.1% (w/v) to about 20% (w/v), preferably about 1% (w/v) to about 4% (w/v), and more preferably about 2% (w/v) to about 3% (w/v).

Disclosed is the use of thidiazuron in methods for the preparation of transgenic strawberry plants comprising contacting strawberry explants with thidiazuron.

The invention further encompasses strawberry plants produced by any of the above described methods.

The features and details of the invention will be more fully appreciated in light of the following detailed description of the invention.

DEFINITIONS

The following definitions are provided as an aid to understanding the detailed description of the present invention.

"Adaxial" refers to the upper surface of an expanded leaf or petal.

"Auxin" refers to a class of plant hormones that promotes growth in plant cells and tissues by elongation rather than by the multiplication of cells. The auxin induces cell elongation by causing the cell wall to soften at the "growing" end of the cell.

"Callus" refers to a proliferating mass of plant cells or tissue in vitro.

"Crown" refers to the region of a seed plant at which the stem and root merge.

"Cytokinin" refers to a class of plant hormones whose principle functions are the induction of cell division (cytokinesis) and the regulation of tissue differentiation.

"Explant" refers to a piece of tissue or an organ removed from a plant to start a plant cell culture.

The phrase "low light conditions" refers to a light intensity of about 0 $\mu$Einsteins m$^{-2}$ sec$^{-1}$ to about 40 $\mu$Einsteins m$^{-2}$ sec$^{-1}$.

"Node" refers to the position on a stem at which one or more leaves are attached.

"Nucleic acid" refers to deoxyribonucleic acid (DNA) and ribonucleic acid (RNA).

"Runner" refers to strawberry stem with long internodes.

"Sheath" refers to any leaflike structure surrounding an organ or plant part, e.g. leaf sheath.

"Transformation" refers to the introduction of nucleic acid into a recipient host or hosts. "Host" or "hosts" refers to entire plants, plantlets, or plant parts such as plant cells, protoplasts, calli, roots, tubers, propagules, seeds, seedlings, pollen, and plant tissues.

"Transgenic" refers to organisms into which new nucleic acid sequences are added.

DETAILED DESCRIPTION OF THE INVENTION

The present invention involves improved methods for the transformation and preparation of transgenic strawberry plants.

An appropriate DNA sequence is selected for introduction into the strawberry plant cells. The sequence typically contains a gene of interest, a promoter functional to direct transcription of the gene, and a selectable marker to facilitate identification of the transformed plant cells. Examples of selectable markers include, but are not limited to, the NPT II, HPT, and EPSPS genes.

Expression of the selectable marker confers resistance to a selective agent. Growth of plant cells on medium containing the selective agent allows phenotypic differentiation of the transgenic and non-transgenic plant cells. Cells lacking the selectable marker are unable to grow in the presence of the selective agent.

Explants are obtained from either strawberry cultures grown in micropropagation media or from strawberry sheath leaves. The explants are placed onto preculture plates and placed under low light conditions prior to transformation.

Co-culturing of leaf explants and a liquid culture of *Agrobacterium tumefaciens* bacteria harboring the DNA plasmid is performed for approximately 30 minutes. The bacterial culture is aspirated, and the explants are stored under low light conditions at approximately 22° C. for about three days to continue co-culturing with the *Agrobacterium tumefaciens*.

Explants are moved to delay medium for about three days at approximately 22° C. The samples are kept under low light conditions during the delay period.

The samples are transferred onto selection medium containing about 20 g/L glucose and appropriate selective agents, and cultured for about three weeks in low light. Subcultures are performed approximately every three weeks. Transformed explants produce green shoots and green callus. Explants containing green shoots and callus are selected for further processing.

Once the actively growing tissue regenerated from the explant unit has grown to about triple its original size, the individual shoots are placed on elongation medium. This step may take between three and six weeks. Shoots are rooted on rooting medium for about two to three weeks.

Shoots are potted in soil, preferably Sunshine mix #1 to grow into strawberry plants.

EXPERIMENTAL PROTOCOLS

The following protocols are included to specify conditions, components, and methods involved in the preparation of transgenic strawberry plants. One skilled in the art will recognize that changes to the compositions, concentrations, times, and steps may be made without deviating from the scope and spirit of the invention. Two general strawberry transformation methods are disclosed: strawberry sheath leaf transformation and strawberry micropropagation transformation. Where alternative compositions or methods are available, they are indicated by different letters, e.g. media A, media B, method A, method B.

Strawberry Sheath Leaf Transformation Protocol

Leaf Collection

Stock plants are grown in the greenhouse and growth chamber. Runner leaves of approximately 5–7 mm in length which are still enclosed in the sheath are collected. The sheaths can be easily pinched off the runners of the stock plants. These sheaths are collected each morning and are placed in water and kept in a refrigerator until they are sterilized for a given experiment.

Leaf Sterilization

The leaves are surface sterilized by rinsing the sheaths in water in a sterile bottle. The leaves are then briefly immersed in approximately 70% (volume/volume, v/v) ethanol in the bottle. The ethanol is removed and the leaves are soaked in approximately 5% (v/v) bleach with gentle agitation for about 10 minutes. The bleach is poured off and the leaves are rinsed thoroughly about 3–4 times with sterilized distilled water.

Explant Preparation/Preculture

This procedure is performed using a dissecting microscope. The sheath is placed in a petri plate with droplets of sterile water. The sheath is removed and the leaf is pulled out using sterile forceps. The three leaflets are then separated. Each leaflet is dissected longitudinally, through the midrib, into two pieces. Approximately 25 to 30 explants per plate are positioned with the adaxial surface down onto regeneration medium (Table 1). The plates are wrapped in aluminum foil and incubated under low light conditions for about 6 days at about 22° C.

TABLE 1

Regeneration medium

| Component | Concentration |
| --- | --- |
| MS salts/B5 vitamins (Sigma M0404) | 4.4 g/L |
| Thidiazuron | 10 µM |
| Indoleacetic acid | 2.5 µM |
| Glucose | 20 g/L |

Agrobacterium Preparation

Agrobacterium is streaked from a frozen stock onto an LB plate containing spectinomycin, streptomycin, chloramphenicol, and kanamycin (denoted ssck, Table 2) four days prior to inoculation. On the day before inoculation, a liquid culture is started using a 10 µL loop of Agrobacterium and inoculating a tube containing 2 µL of 2YT medium (16 g/L peptone, 10 g/L yeast extract, and 5 g/L sodium chloride) containing spectinomycin, streptomycin, chloramphenicol, and kanamycin. The tubes are placed on a spinner overnight. In the morning of the day of inoculation, 1 tube (2 mL) of Agrobacterium is combined with 20 mL of 2YT medium (without antibiotics) in a sterile flask. The flask is placed on a shaker for about 6 hours. This Agrobacterium culture is used as the inoculum. The optical density at 660 nanometers is measured using a spectrophotometer. The final optical density of the inoculum should be about 1.0. If the reading is higher, this culture may be diluted with liquid TXD medium (Table 3) supplemented with 200 µM acetosyringone and 100 mM galacturonic acid in order to achieve a final density equivalent to an optical density of about 1.0.

TABLE 2

LB/ssck medium

| Component | Concentration |
| --- | --- |
| Sodium chloride | 10 g/L |
| Tryptone | 10 g/L |
| Yeast extract | 5 g/L |
| Difco bacto agar | 15 g/L |
| Spectinomycin | 100 mg/L |
| Chloramphenicol | 25 mg/L |
| Kanamycin | 50 mg/L |
| pH adjusted to 7.0 | |

TABLE 3

TXD medium

| Component | Concentration |
| --- | --- |
| MS salts (GIBCO BRL 11154) | 4.3 g/L |
| Gamborg B5 vitamins (500X)(Sigma G1019) | 1 mL/L |
| Phenoxyacetic acid | 4 mg/L |
| Kinetin | 5 µg/L |
| Sucrose | 30 g/L |
| pH adjusted to 5.7 | |

Inoculation/Co-Culture

After the six day pre-culture period, each leaf is placed in a petri dish with a droplet of sterile water and cut into two pieces. The edges are trimmed, and any brown or dead tissue is discarded. Care must be exercised when cutting to keep track of the adaxial surface. This leaf tissue is then incubated in the petri dish with the Agrobacterium suspension for about 25–30 minutes. Enough Agrobacterium suspension is added to just cover explants to maintain an adaxial down orientation, without the explants floating. The tissue is blotted on a sterile WHATMAN filter paper (WHATMAN is a registered trademark of Whatman International, Ltd., Hillsboro, Oreg.) and placed on co-culture plates. Co-culture plates consist of 1X MS basal salts and 1X Gamborg B5 vitamins, 10 µM thidiazuron, 10 µM indoleacetic acid, and 2% glucose (w/v) medium, two sterile filter papers, and a liquid overlay of TXD medium (Table 3) supplemented with 200 µM acetosyringone and 100 mM galacturonic acid. The plates are then wrapped in foil and incubated under low light conditions for about 3 days at approximately 22° C. All tissue is cultured under these conditions unless noted.

Delay

After the approximately 3 day co-culture period, the explants are transferred to a delay medium (Table 4 or Table 5). The explants are incubated on these plates under low light conditions for three days at approximately 22–24° C.

TABLE 4

Delay medium A

| Component | Concentration |
|---|---|
| MS salts/MS vitamins (Sigma M0404) | 4.4 g/L |
| Glucose | 20 g/L |
| Washed agar | 8 g/L |
| Thidiazuron | 2.3 mg/L |
| Indoleacetic acid | 1.75 mg/L |
| Timentin | 500 mg/L |
| Cefotaxime | 100 mg/L |
| pH adjusted to 5.7 | |

TABLE 5

Delay medium B

| Component | Concentration |
|---|---|
| MS salts/MS vitamins (Sigma M0404) | 4.4 g/L |
| Glucose | 20 g/L |
| Phytagel | 4 g/L |
| Thidiazuron | 2.3 mg/L |
| Indoleacetic acid | 1.75 mg/L |
| Ticarcillin | 500 mg/L |
| Cefotaxime | 100 mg/L |
| pH adjusted to 5.7 | |

Selection Method A

After the three day delay period, the leaves are transferred to selection medium A (Table 6). The explants are maintained at about 22° C. and are cultured in the light (approximately 20–40 $\mu$Einsteins m$^{-2}$ sec$^{-1}$). The explants are subcultured to fresh medium every three weeks. Once a shoot clump has about tripled in size, individual shoots can be transferred to elongation medium A (Table 7). The elongation step may take 3–6 weeks. Shoots are rooted on MS medium supplemented with 0.37 mg/L indolebutyric acid, 500 mg/L Timentin, and 100 mg/L Cefotaxime (rooting medium A, Table 8). The rooting step may take 2–3 weeks. Shoots are potted into 6-pack containers of Sunshine mix #1 (80% peat) (Sungrow Horticultural, Bellvue, Wash.). The containers are placed into a misting tent on trays with dome lids for 3 days. Subsequently, the dome lids are tilted halfway to allow for airflow for 3 more days. The dome lid is removed after 6 days and plants stay under the misting tent for an additional 10 to 15 days. Plants are then taken out and set on a bench for 7 days and transplanted into 6 inch pots of 25% of each: peat, sand, pumice, and redwood mulch. Plants are misted until they are taken out of the misting tent. Greenhouse day temperatures range from about 20–24.5° C. and the night temperatures are about 10–14.5° C. There is no artificial light, and light intensity is decreased from the end of May to the end of September by use of a shade cloth.

TABLE 6

Selection and regeneration medium A

| Component | Concentration |
|---|---|
| MS salts/MS vitamins (Sigma M0404) | 4.4 g/L |
| Glucose | 20 g/L |
| Washed Agar | 8 g/L |
| Thidiazuron | 2.3 mg/L |
| Indoleacetic acid | 1.75 mg/L |

TABLE 6-continued

Selection and regeneration medium A

| Component | Concentration |
|---|---|
| Timentin | 500 mg/L |
| Cefotaxime | 100 mg/L |
| Kanamycin | 50 mg/L |
| pH adjusted to 5.7 | |

Regeneration Medium Lacks Kanamycin

TABLE 7

Elongation medium A

| Component | Concentration |
|---|---|
| MS salts/MS vitamins (Sigma M0404) | 4.4 g/L |
| Glucose | 20 g/L |
| Washed agar | 8 g/L |
| Timentin | 500 mg/L |
| Cefotaxime | 100 mg/L |
| Indoleacetic acid | 0.45 mg/L |
| Galacturonic acid | 2.5 mg/L |
| Kanamycin | 50 mg/L |
| pH adjusted to 5.7 | |

TABLE 8

Rooting Medium A

| Component | Concentration |
|---|---|
| MS salts (Sigma 0153) | 2.2 g/L |
| MS vitamins (Sigma M3900) | 1 mL/L |
| MgSO$_4$ · 7 H$_2$O | 0.2797 g/L |
| CaCl$_2$ · 2 H$_2$O | 0.2739 g/L |
| KH$_2$PO$_4$ | 0.5950 g/L |
| H$_3$BO$_3$ | 18.6 mg/L |
| NaMoO$_4$ · 2 H$_2$O | 0.7 mg/L |
| Iron stock | 5 mL/L |
| Myo-inositiol | 100 mg/L |
| Ascorbic acid | 100 mg/L |
| Indolebutyric acid | 0.37 mg/L |
| Timentin | 500 mg/L |
| Cefotaxime | 100 mg/L |
| Glucose | 20 g/L |
| Washed agar | 8 g/L |
| pH adjusted to 5.7 | |

Selection Method B

After the three day delay period, the leaves are transferred to selection medium B (Table 9). The explants are maintained at about 24° C. and are cultured in the light (approximately 20–40 $\mu$Einsteins m$^{-2}$ sec$^{-1}$). The explants are subcultured to fresh medium every three weeks. Once a shoot clump has about tripled in size, individual shoots can be transferred to elongation medium B (Table 10). The elongation step may take 3–6 weeks. Shoots are rooted on MS medium supplemented with 0.37 mg/L indolebutyric acid, 500 mg/L Ticarcillin, and 100 mg/L Cefotaxime (rooting medium B, Table 11). The rooting step may take 2–3 weeks. Shoots are potted in moistened Metro Mix 350 soil in small pots (1.5" square). They are placed in a tray and covered with a clear plastic dome to ensure adequate humidity. They are placed in a growth chamber of 27° C. day and 21° C. night, and a 16/8 hour light cycle. The plants are watered daily. After about 5 to 7 days, the lid is partially cracked. After another 5 to 7 days, the lid is completely removed if the plants show new growth.

TABLE 9

Selection and regeneration medium B

| Component | Concentration |
|---|---|
| MS salts/MS vitamins (Sigma M0404) | 4.4 g/L |
| Glucose | 20 g/L |
| Phytagel | 4 g/L |
| Thidiazuron | 2.3 mg/L |
| Indoleacetic acid | 1.75 mg/L |
| Ticarcillin | 500 mg/L |
| Cefotaxime | 100 mg/L |
| Kanamycin | 50 mg/L |
| pH adjusted to 5.7 | |

Regeneration Medium Lacks Kanamycin

TABLE 10

Elongation medium B

| Component | Concentration |
|---|---|
| MS salts/MS vitamins (Sigma M0404) | 4.4 g/L |
| Sucrose | 20 g/L |
| Washed agar | 8 g/L |
| Ticarcillin | 500 mg/L |
| Cefotaxime | 100 mg/L |
| Indoleacetic acid | 0.45 mg/L |
| Galacturonic acid | 2.5 mg/L |
| Kanamycin | 50 mg/L |
| pH adjusted to 5.7 | |

TABLE 11

Rooting Medium B

| Component | Concentration |
|---|---|
| MS salts (Sigma 0153) | 2.2 g/L |
| MS vitamins (Sigma M3900) | 1 mL/L |
| $MgSO_4 \cdot 7 H_2O$ | 0.2797 g/L |
| $CaCl_2 \cdot 2 H_2O$ | 0.2739 g/L |
| $KH_2PO_4$ | 0.5950 g/L |
| $H_3BO_3$ | 18.6 mg/L |
| $NaMoO_4 \cdot 2H_2O$ | 0.7 mg/L |
| Iron stock | 5 mL/L |
| Myo-inositiol | 100 mg/L |
| Ascorbic acid | 100 mg/L |
| Indolebutyric acid | 0.37 mg/L |
| Ticarcillin | 500 mg/L |
| Cefotaxime | 100 mg/L |
| Sucrose | 20 g/L |
| Washed agar | 8 g/L |
| pH adjusted to 5.7 | |

Strawberry Micropropagation Transformation Protocol A

Plant Material

In vitro strains BHN FL90031-30 or BHN 92664-501 (CA-adapted) strawberry cultures are grown in presterilized Magenta GA7 boxes (Magenta Co., Chicago, Ill.) containing micropropagation medium (Table 12). Each unit of tissue contains two to three apical meristems, and two units are placed in each jar. The cultures are then incubated at about 22° C., with cool white light with 16/8 photoperiod at about 34–40 $\mu$Einsteins $m^{-2}$ $sec^{-1}$. About every four weeks, each unit of tissue is subdivided into two to four clumps and placed on fresh media of the same composition. Ideal stock material for explanting is available at two to three weeks after the last subculture.

TABLE 12

Micropropagation Medium

| Component | Concentration |
|---|---|
| MS salts (Sigma 0153) | 2.2 g/L |
| MS vitamins (Sigma M3900) | 1 mL/L |
| $MgSO_4 \cdot 7 H_2O$ | 0.2797 g/L |
| $CaCl_2 \cdot 2 H_2O$ | 0.2739 g/L |
| $KH_2PO_4$ | 0.5950 g/L |
| $H_3BO_3$ | 18.6 mg/L |
| $NaMoO_4 \cdot 2 H_2O$ | 0.7 mg/L |
| Iron stock | 5 mL/L |
| Myo-inositiol | 100 mg/L |
| Ascorbic acid | 100 mg/L |
| N6-benzylaminopurine | 1 mg/L |
| Indolebutyric acid | 0.37 mg/L |
| Sucrose | 30 g/L |
| Washed agar | 8 g/L |
| pH adjusted to 5.8 | |

Agrobacterium preparation

Four days prior to co-cultivation, *Agrobacterium tumefaciens* strain ABI was streaked from a frozen glycerol stock onto a LB plate containing 75 mg/L kanamycin, 100 mg/L spectinomycin and 25 mg/L chloramphenicol. *Agrobacterium tumefaciens* strain LBA4404 were streaked from a frozen glycerol stock AB plate (AB media supplemented with 15 g Difco Bacto Agar, Table 13) containing 150 g/L streptomycin, 100 mg/L gentamycin and 100 mg/L kanamycin. Twenty-four hours prior to co-cultivation single colonies were placed into 5 mL of AB media (Table 13) for ABi strain or 5 mL of MG/L media (Table 14) for LBA4404 strains. Cultures were grown overnight at 30° C., 200 rpm agitation.

TABLE 13

AB media

| Component | Amount |
|---|---|
| 20X AB Stocks [120 g/L $K_2HPO_4$, 46 g/L $NaH_2PO_4 \cdot H_2O$, 40 g/L $NH_4Cl$, 6 g/L KCl] | 50 mL |
| 1 M $MgSO_4$ | 1 mL |
| 0.1 M $CaCl_2$ | 1 mL |
| 20% Glucose (w/v) | 25 mL |
| $FeSO_4 \cdot 7 H_2O$ (0.25 mg/mL) | 10 mL |

TABLE 14

MG/L media

| Component | Concentration |
|---|---|
| Mannitol | 5 g/L |
| L-glutamic acid | 1 g/L |
| $KH_2PO_4$ | 0.25 g/L |
| NaCl | 0.10 g/L |
| $MgSO_4 \cdot 7 H_2O$ | 0.10 g/L |
| Biotin | 1 $\mu$g/L |
| Tryptone | 5 g/L |
| Yeast extract | 2.5 g/L |
| pH adjusted to 7.0 | |

Explant Inoculation.

Explanting and Pre-Culture Steps

Small folded leaves about 2–4 mm in length possessing a vibrant green, glassy appearance are excised at the petiole. They are placed into a petri dish containing about 1–1.5 mL of sterile water and a sterilized WHATMAN filter paper. The basal portion of the leaves is removed with a single cut such that 3 leaflets are produced from each leaf. The leaflets (explants) are placed onto the preculture plates (Table 15). The preculture plates are prepared using solid medium and pipetting 1 mL of TXD liquid medium which has been supplemented with 200 µM acetosyringone and 100 mM galacturonic acid onto the solid plate. Two sterilized WHATMAN filter papers are placed onto the plate. Approximately 50 explants are placed onto each preculture plate. The plates are placed under low light conditions for about three days by placing in an aluminum foil covered box.

TABLE 15

Preculture/co-culture medium with overlay

| Component | Concentration |
| --- | --- |
| MS salts/MS vitamins (Sigma M0404) | 0.44 g/L |
| Glucose | 30 g/L |
| Washed agar | 8 g/L |
| Thiadazuron | 2.2 mg/L |
| Indoleacetic acid | 1.75 mg/L |
| Acetosyringone | 39.28 mg/L |
| Galacturonic acid (100 mM) | 4 mL |
| pH adjusted to 5.7 | |

The overlay is 1 mL/plate of TXD liquid medium containing 200 µM acetosyringone, 100 mM galacturonic acid, and 2 sterile WHATMAN 8.5 cm filter papers.

Inoculation and Co-Culture Steps

The Agrobacterium suspension is diluted to $5 \times 10^8$ bacteria/mL with AB or MG/L media as appropriate for the strain just immediately prior to use. The explants are removed from the preculture plate and allowed to sit in 5 mL of bacterial suspension for 5 minutes. The explants are then removed from the bacterial suspension and blotted dry on sterile paper towels and placed back on the preculture plate. The explants are spread out uniformly adaxial side down so that all are in good contact with the filter paper and are not overlapping. These plates are then co-cultured under low light conditions for an additional 3 days.

Tissue Selection and Regeneration

The explants are moved to delay medium (Table 4) for 3 days, adaxial side down. The explants are stored under low light conditions during the delay period.

After the three day delay, the explants (about 50 per plate) are transferred adaxial side down onto selection medium A (Table 6) and are cultured for about 3 weeks in the light (20–40 µEinsteins $m^{-2}$ $sec^{-1}$). After about 3 weeks, the explants are placed on selection medium B (Table 16). Subculture s are performed every 3 weeks. By 6 weeks, transformed explants will produce green shoots and green callus. Only explants which contain this shooting material and green callus should be moved. If the explants associated with the shoots and green callus are still green and healthy, then the entire explant should be moved together with the regenerating material. By 9 to 12 weeks, green actively growing shoot units can be picked from the explants and placed by themselves on selection medium B (Table 16). Each actively dividing unit represents an independent event. Once the unit has tripled in size, individual shoots can be placed on elongation medium (Table 6). This step may take three to six weeks. Shoots are rooted on rooting medium (Table 7). This step requires approximately two to three weeks.

TABLE 16

Selection and regeneration medium B

| Component | Concentration |
| --- | --- |
| MS salts/MS vitamins (Sigma M0404) | 4.4 g/L |
| Glucose | 30 g/L |
| Washed agar | 8 g/L |
| Thiadazuron | 3.4 mg/L |
| Indoleacetic acid | 0.45 mg/L |
| Timentin | 500 mg/L |
| Cefotaxime | 100 mg/L |
| Kanamycin | 50 mg/L |
| pH adjusted to 5.7 | |

Regeneration Medium Lacks Kanamycin

Shoots are potted into 6-pack containers of Sunshine mix #1 (80% peat). The containers are placed into a misting tent on trays with dome lids for 3 days. Subsequently, the dome lids are tilted halfway to allow for airflow for 3 more days. The dome lid is removed after 6 days and plants stay under the misting tent for an additional 10 to 15 days. Plants are misted until they are taken out of the misting tent. Plants are then taken out and set on a bench for 7 days and transplanted into 6 inch pots of 25% of each: peat, sand, pumice, and redwood mulch. Greenhouse day temperatures range from about 20–24.5° C. and the night temperatures are about 10–14.5° C. There is no artificial light, and light intensity is decreased from the end of May to the end of September by use of a shade cloth.

Strawberry Micropropagation Transformation Protocol B

Plant Material

In vitro Redcoat strawberry cultures are grown in presterilized glass containing micropropagation medium (Table 12). Each unit of tissue contains two to three apical meristems, and two units are placed in each jar. The cultures are then placed in a warm room of 24° C., with cool white light with a 16/8 photoperiod at 34–40 µEinsteins $m^{-2}$ $sec^{-1}$. About every four weeks, each unit of tissue is subdivided into two to four clumps and placed on fresh media of the same composition. Ideal stock material for explanting is available at about three to four weeks after the last subculture.

Agrobacterium Preparation

Agrobacterium is streaked from a frozen glycerol stock onto an LB/ssck plate (Table 2). Forty-eight hours prior to inoculation, a 10 µL loop of Agrobacterium is placed into 2 mL of YEPssck (Table 17) and placed on an orbital shaker for 24 hours. After 24 hours (1 day prior to inoculation), 0.4 mL of the suspension is placed into 2 mL of fresh YEPssck. Three tubes are made for each construct. The tubes are returned to the orbital shaker for 7–8 hours. After the 7–8 hours, the 6 mL from the three tubes for each construct is pipetted into a presterilized 250 mL flask containing 50 mL of AB media (Table 13).

TABLE 17

YEPssck media

| Component | Concentration |
| --- | --- |
| Yeast extract | 10 g/L |
| Peptone | 10 g/L |
| Spectinomycin | 100 mg/L |
| Streptomycin | 100 mg/L |
| Chloramphenicol | 25 mg/L |
| Kanamycin | 50 mg/L |

Explant Inoculation.
Explanting and Pre-Culture Steps

Small folded leaves about 2–4 mm in length possessing a vibrant green, glassy appearance are excised at the petiole. They are placed into a petri dish containing about 2–4 mL of sterile water. The leaves are diced with a scalpel such that each leaf is cut into multiple pieces. The water is removed and the diced leaves (explants) are placed onto the preculture plates (Table 18). The preculture plates are prepared using solid medium and pipetting 2 mL of TXD liquid medium which has been supplemented with 200 μM acetosyringone and 100 mM galacturonic acid onto the solid plate. Two sterilized WHATMAN filter papers are placed onto the plate. Approximately 80 explants are placed onto each preculture plate. The plates are placed under low light conditions for about three days by placing in an aluminum foil covered box, or by being wrapped in aluminum foil.

TABLE 18

Preculture/co-culture medium with overlay

| Component | Concentration |
|---|---|
| MS salts/MS vitamins (Sigma M0404) | 0.44 g/L |
| Glucose | 30 g/L |
| Phytagel | 4 g/L |
| Thiadazuron | 2.2 mg/L |
| Indoleacetic acid | 1.75 mg/L |
| Acetosyringone | 39.28 mg/L |
| Galacturonic acid | 1 mM |
| pH adjusted to 5.7 | |

The overlay is 2 mL/plate of TXD liquid medium containing 200 μM acetosyringone, 100 mM galacturonic acid, and 2 sterile WHATMAN 8.5 cm filter papers.

Inoculation and Co-Culture Steps

The flasks of Agrobacterium suspension are removed from the shaker. The bacteria is diluted with liquid plant medium to achieve a final optical density reading of 1.2–1.4 at 600 nm. Eight mL of this bacterial suspension is pipetted over the explants on the preculture plate. The explants should be thoroughly wet. The plates can be tilted and the explants moved to sit in the collected bacterial volume, but this is not critical for successful transformation. The explants should contact the Agrobacterium for at least about 30 minutes. The Agrobacterium is subsequently aspirated off of the plates. The explants are spread out uniformly such that all are in good contact with the filter paper, and are not overlapping. The plates are then returned to the dark for an additional three days for co-culture.

Tissue Selection and Regeneration

The explants are moved to delay medium (Table 5) for three days. The adaxial side (upper side) is placed in a down orientation. The explants are also kept in the dark during the delay period.

After the delay period, the explants (about 25 per plate) are transferred adaxial side down onto selection medium (Table 9) and are cultured for about 3 weeks in the light (20–40 μEinsteins m$^{-2}$ sec$^{-1}$). After about 3 weeks, the explants are placed on a more stringent selection medium (Table 19). Subcultures are performed every three weeks. By 6 weeks, transformed explants will produce green shoots and green callus. Only explants which contain this shooting material and green callus should be moved. If the explants associated with the shoots and green callus are still green and healthy, then the entire explant should be moved together with the regenerating material. By 9 to 12 weeks, green actively growing shoot units can be picked from the explants and placed by themselves on stringent selection medium (Table 19). Each actively dividing unit represents an independent event. Once the unit has about tripled in size, individual shoots may be placed on elongation medium (Table 10). This elongation step to generate shoots may take three to six weeks. Shoots are rooted on rooting medium (Table 11) lacking N6-benzylaminopurine. This rooting step requires approximately two to three weeks.

TABLE 19

Selection medium

| Component | Concentration |
|---|---|
| MS salts/B5 vitamins (Sigma M04040) | 4.4 g/L |
| Glucose | 30 g/L |
| Phytagel | 4 g/L |
| Thiadazuron | 34 mg/L |
| Indoleacetic acid | 0.45 mg/L |
| Ticarcillin | 500 mg/L |
| Cefotaxime | 100 mg/L |
| Kanamycin | 50 mg/L |
| pH adjusted to 5.7 | |

Shoots are potted into Metro Mix 350 soil. Planted shoots are placed in a tray and covered with a clear plastic dome to ensure humidity. They are placed in a growth chamber set at 27 night/21 day with a 16/8 light/dark cycle. The plants are watered daily. After five to seven days, the lid is gradually cracked. After an additional five to seven days, the lid is completely removed if the plants show new growth.

Combined Elongation and Rooting Steps

Elongation and rooting steps may be performed concurrently using a modified media composition. Overall shoot growth is enhanced with the combination of 1 mg/L galacturonic acid and 0.5 mg/L indolebutyric acid (Table 20). This combined procedure of elongation and rooting requires approximately three to six weeks from transfer of explants from the delay medium. The combination of elongation and rooting steps results in a more streamlined procedure for the preparation of transgenic strawberries.

TABLE 20

Simultaneous elongation and rooting medium

| Component | Concentration |
|---|---|
| MS salts/B5 vitamins (Sigma M04040) | 4.4 g/L |
| Sucrose | 20 g/L |
| Washed agar | 8 g/L |
| Ticarcillin | 500 mg/L |
| Cefotaxime | 100 mg/L |
| Galacturonic acid | 1 mg/L |
| Indolebutyric acid | 0.5 mg/L |
| pH adjusted to 5.7 | |

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1
Effect of Explant Type on Regeneration Using the Greenhouse Protocol Four commercial strawberry genotypes were tested to determine which type of leaf generated the highest number of shoots per explant. Young leaves approximately 5–7 mm long from Pajaro, Osa Grande, Grace and Selva strawberries were excised either from the crown, runner tip, or first node of mother plants and surface sterilized. Each leaf was then cut and placed adaxial surface down on shoot induction medium and precultured for six days. The leaves were co-cultured with Agrobacterium harboring a binary vector pMON15737 that contained a β-glucuronidase (GUS) gene, a kanamycin resistance selectable marker gene (NOS128/NPTII/NOS), and transferred to delay medium. The explants were then incubated under low light conditions for three days at approximately 22° C. Afterwards, the explants were placed in selection medium A and cultured for four weeks. Transformation was confirmed by histochemical analysis of green calli and shoots for GUS activity, and by Southern blot analysis. Table 21 displays the number of shoots produced per explant after four weeks of culture. The runner leaves in all four commercial strawberries produced the highest number of shoots per explant.

TABLE 21

| Genotype | Explant Leaves | Total Explants | Mean No. Shoots/Explant |
| --- | --- | --- | --- |
| Pajaro | Runner | 86 | 40 |
| | Crown | 28 | 23 |
| | Node | 18 | 10 |
| Osa Grande | Runner | 72 | 27 |
| | Crown | 74 | 24 |
| | Node | 20 | 22 |
| Grace | Runner | 16 | 9 |
| | Crown | 49 | 6 |
| Selva | Runner | 16 | 11 |
| | Crown | 49 | 5 |

Example 2
Effect of Kanamycin Delay on Regeneration

Micropropagated strawberry explants were co-cultivated with *Agrobacterium tumefaciens*. The explants were transferred to delay medium and incubated under low light conditions for three days at approximately 22° C. Afterwards, the explants were placed in selection medium B containing 50 mg/L of kanamycin and selected for kanamycin resistant calli. Table 22 shows that a delay of kanamycin selection improves the transformation efficiency by Agrobacterium.

TABLE 22

| Days of Delay | # of Explants | # of Kanamycin Resistant Calli |
| --- | --- | --- |
| 0 | 660 | 19 |
| 3 | 665 | 74 |

Example 3
Effect of Glucose on Shoot Regeneration When Using Micropropagated Strawberry Cultures Utilizing the methods previously described in Example 2 and in the experimental protocols section, explants derived from micropropagated strawberry cultures were cultured in co-cultivation, delay, selection, elongation and rooting media containing 2% sucrose (w/v) or 2% glucose (w/v) to compare the efficacy of different carbon sources on shoot production. Table 23 demonstrates that glucose greatly improves shoot production in comparison to sucrose when using micropropagated strawberry cultures.

TABLE 23

| Carbohydrate | Total # Explants | # of Regenerating Explants | % of Regenerating Explants | Average of % Regenerating Explants |
| --- | --- | --- | --- | --- |
| Sucrose | 31 | 0 | 0 | |
| | 36 | 1 | 3 | |
| | 23 | 8 | 34 | |
| | 24 | 14 | 58 | 23% |
| Glucose | 30 | 18 | 60 | |
| | 27 | 18 | 66 | |
| | 26 | 26 | 100 | |
| | 19 | 12 | 63 | 72% |

Example 4
Effect of Glucose on Shoot Regeneration When Using Strawberry Sheath Leaves Explants derived from the runner leaves of Redcoat strawberries were cultured in the presence of either sucrose or glucose to compare the efficacy of different carbon sources on shoot production, utilizing the methods previously described in Example 1 and in the experimental protocols section. Table 24 demonstrates that glucose improves shoot production in comparison to sucrose when using strawberry sheath leaves.

TABLE 24

| Glucose | Sucrose | Number of shoots generated per explant |
| --- | --- | --- |
| 1% | 0 | 300 |
| 2% | 0 | 600 |
| 3% | 0 | 90 |
| 0 | 1% | 90 |
| 0 | 2% | 300 |
| 0 | 3% | 300 |

Example 5
Comparison of Glucose, Sucrose, and Fructose as Carbohydrate Sources A comparison of carbohydrate sources in the micropropagation and regeneration media was performed. All sugars were used at 30 g/L.

Both fructose and glucose demonstrated improved regeneration properties as compared to sucrose (Table 25).

TABLE 25

| Treatment[a] | Events | # of regenerating clumps[b] | # of events producing callus | Weight of total tissue[c] | Avg. weight of tissue per event |
| --- | --- | --- | --- | --- | --- |
| Sucrose to sucrose | 80 | 2 (2.5%) | 44 (55%) | 3.27 g | 40.9 mg |
| Sucrose to glucose | 160 | 14 (8.8%) | 136 (85%) | 10.87 g | 67.9 mg |
| Fructose to fructose | 160 | 54 (33.8%) | 148 (93%) | 26.87 g | 167.9 mg |
| Glucose to glucose | 160 | 80 (50%) | 155 (97%) | 26.86 g | 167.9 mg |

[a]First sugar listed was the component in the micropropagation media. Second sugar corresponds to component in regeneration media.

TABLE 25-continued

| Treatment[a] | Events | # of regenerating clumps[b] | # of events producing callus | Weight of total tissue[c] | Avg. weight of tissue per event |
|---|---|---|---|---|---|

[b]This number represents clumps from single origins. Multiple clumps growing from one point was counted as one. Different clumps from the same callus were counted individually.
[c]This number represents all tissue on plates.

Example 6
Effect of Fructose on Strawberry Regeneration and Transformation

Folded leaf explants from in vitro shoots of FL9003 1-30 were compared for regeneration ability on three carbon sources, sucrose, fructose and glucose. Eighty explants for each treatment were placed (adaxial side to medium) directly on regeneration medium A (Table 6) for three weeks, transferred to regeneration medium B (Table 16) for 3 weeks, and then transferred to fresh regeneration medium B (Table 16) for two additional weeks. Explants were evaluated for the formation of shoots. Three percent glucose produced the most regeneration with 90% of the explants forming shoots. Seventy-five percent of the explants on fructose regenerated while only 25% of the explants on 3% sucrose regenerated.

The construct pCGN8035 was cocultivated with FL9003 1-30 using the in vitro leaf protocol except that 3% fructose was substituted in each medium for glucose. Seven hundred explants were cut and cocultivated. Forty-six plants were rooted and sent to the greenhouse for a transformation rate of 6.57%.

Example 7
Effect of Explant Type on Regeneration Response

Explant tissue sources were evaluated in the micropropagation transformation method for their effects on regeneration. Folded leaves, unfolded leaves, and petioles were compared as explant sources, and three different media were used: regeneration media (Table 6) with 10 μM TDZ and 2.5 μM IAA (medium #1), 15 μM TDZ and 2.5 μM IAA (medium #2), and 20 μM TDZ and 2.5 μM IAA (medium #3). These results indicate that unfolded leaves are superior to the other tested explant sources.

TABLE 26

Explant tissue sources

| Tissue type | % Regeneration in medium #1 | % Regeneration in medium #2 | % Regeneration in medium #3 |
|---|---|---|---|
| Folded leaves | 25 | 35 | 49 |
| Unfolded leaves | 8 | 5 | 25 |
| Petioles | 0 | 0 | 0 |

Example 8
Effect of Cytokinin on Regeneration Response

Non-transgenic explants by the micropropagation method using folded leaves were regenerated on regeneration medium (Table 6) containing either thidiazuron (TDZ) or benzyladenine (BA) at 10 μM, with other components staying constant. The use of TDZ in the regeneration media resulted in over twice the percent regeneration of the explants.

TABLE 27

Comparison of TDZ and BA effects on regeneration

| Cytokinin | Number of explants | Number Regenerated | Percent regenerated | Average of % regenerated |
|---|---|---|---|---|
| TDZ | 78 | 63 | 80 | |
| | 21 | 10 | 48 | |
| | 55 | 19 | 35 | 54 |
| BA | 134 | 19 | 14 | |
| | 13 | 5 | 38 | |
| | 18 | 2 | 11 | 21 |

Example 9
Strawberry Southern Blot Data

Genomic DNA was prepared from Florida 90031-30 transgenic strawberry lines. The DNA was digested with a restriction endonuclease to liberate fragments of various lengths and then separated by electrophoresis in an agarose gel. The digested, size-fractionated DNA was transferred to a nylon membrane by capillary blotting. A radioactive probe was prepared from plasmid DNA that would hybridize to DNA fragments containing binary vector sequences joined to plant DNA sequences at the right or left T-DNA border. The number of transgene insertion sites was estimated from the number of hybridizing bands observed on X-ray film exposed to the radioactive membrane. A summary of the results is provided below.

Genomic DNA from twelve transgenic strawberry lines containing the transformation vector pCGN8006 (p-eFMV-GUS-nos3') was digested with EcoRI and evaluated with a radioactive probe from the eFMV promoter region. The X-ray film results indicate that eight lines have a single insertion site, one line has two or three insertion sites, and three lines have three insertion sites.

Genomic DNA from eighteen transgenic strawberry lines containing the transformation vector pCGN8012 (p-eBigMac-GUS-nos3') was digested with XbaI and evaluated with a radioactive probe from the FMV enhancer region (corresponding to the "e" or enhancer element of the eBigMac promoter). The X-ray film results indicate that nine lines have a single insertion site, two lines have two insertion sites, one line has three insertion sites, one line has four insertion sites, and five lines could not be determined due to underloading of the amount of genomic DNA on the gel.

Genomic DNA from sixteen transgenic strawberry lines containing the transformation vector pCGN8015 (p-SRE2-GUS-nos3') was digested with BglII and evaluated with a radioactive probe containing the nos5' promoter and part of the nptII gene. The X-ray film results indicate that nine lines have a single insertion site, two lines have two insertion sites, three lines have three insertion sites, one line has four insertion sites, and one line could not be determined due to crowding of multiple bands (>4).

Using the transformation protocols outlined in this document, in conjunction with the indicated binary vectors and the Abi strain of Agrobacterium, this limited dataset indicates that approximately two-thirds of the transgenic lines have a single insertion site and about one-third have 2 or more insertion sites (usually between two and four).

Example 10
Strawberry GUS Data

Leaves from transgenic strawberry plants were cut into cross-sections and stained for GUS activity in X-Gluc staining solution with 100 mM ascorbic acid, 100 mM sodium phosphate buffer pH 7.0, 1 mg/mL X-Gluc (5-bromo-4-chloro-3-indoyl glucuronide, Sigma #B650), and 0.1% (v/v) TRITON X-100 (TRITON is a registered trademark of Union Carbide Chemicals and Plastics Co., Inc., Danbury, Conn.). After incubation overnight at 37° C., staining intensity was rated on a qualitative scale from "very strong" to "very weak" or "none".

TABLE 28

GUS assays of transgenic strawberry lines

| pCGN 8006 | V. Strong | Strong | Strong/ Medium | Medium | Weak | V. Weak | None |
|---|---|---|---|---|---|---|---|
| # of lines | 3 | 4 | 1 | 1 | 1 | 2 | 0 |
| pCGN 8012 | V. Strong | Strong | Strong/ Medium | Medium | Weak | V. Weak | None |
| # of lines | 0 | 3 | 4 | 6 | 0 | 5 | 0 |
| pCGN 8015 young leaves | Strong | Strong/ Medium | Medium | Medium/ weak | Weak | V. Weak | None |
| # of lines | 0 | 0 | 2 | 2 | 5 | 2 | 5 |
| pCGN 8015 old leaves | V. Strong | Strong | Strong/ Medium | Medium | Medium/ weak | Weak | V. Weak |
| # of lines | 0 | 5 | 4 | 5 | 2 | 0 | 0 |

Non-transgenic strawberries did not display detectable GUS activity.

Example 11

Herbicide Spray Tests

Fifteen transgenic Pajaro strawberry plants from five independent ABI::pMON15737 (FMV/CP4+FMV/GUS) lines were sprayed with the non-specific herbicide ROUNDUP (N-phosphonomethylglycine, ROUNDUP is a trademark of Monsanto Company, St. Louis, Mo.) to evaluate the resistance of the transgenic strawberry plants in comparison to non-CP4 plants. Plants were sprayed with herbicide at a concentration of 24 ounces per acre. Eight non-CP4 transgenic plants were completely dead at four weeks post spray. Excellent vegetative growth was observed on several lines which had been sprayed with herbicide (Table 29). Some lines showed a phenotype which was intermediate, i.e. the plants were producing green leafy growth from the crown, but were paler in color and stunted relative to the unsprayed controls. Expanded leaf samples were collected prior to application of herbicide and evaluated by an ELISA assay for levels of CP4 expression Methods for the analysis of protein expression by immunochemical protocols such as an ELISA are well-known to those skilled in the art (Methods in Molecular Biology, vol. 10, Immunochemical Protocols, edited by Margaret M. Manson, 1992, Humana Press Inc., Totowa, N.J.). In brief, proteins or peptides incorporating antigen sequences are immobilized onto a selected surface, preferably a surface exhibiting a protein affinity such as the wells of a microtiter plate. After washing to remove completely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecifc adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or biological extract to be tested in a manner conducive to immune complex (antigen/antibody) formation. The layered antisera is then allowed to incubate at temperatures on the order of about 25° C. to about 27° C. Following incubation, the antisera-contacted surface is washed to remove nonimmunocomplexed material using a buffer solution such as PBS/TWEEN, or borate buffer.

Following incubation of specific immunocomplexes between the test sample and the bound antigen, and subsequent washing, the immunocomplex formation may be detected by subjecting same to a second antibody having specificity for the first. To provide a detecting means, the second antibody will preferably have an associated enzyme that will generate a color development upon incubating with an appropriate chromogenic substrate, such as alkaline phosphatase or peroxidase-conjugated anti-rabbit IgG for a period of time and under conditions which favor the development if immunocomplex formation.

After incubation with the second enzyme-tagged antibody, and subsequent to washing to remove the unbound material, the amount of label is quantified by incubation with a chromogenic substrate such as p-nitrophenyl phosphate (PNPP) or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation e.g., using a visible spectrophotometer, and comparing the values of the test samples with a curve generated using quantitated protein standards and control test samples.

TABLE 29

Herbicide resistance assays of transgenic strawberry lines

| Line number | Plant number | CP4 level (ppm) | Phentype |
|---|---|---|---|
| 5-1 | 11 | 0.040 | Intermediate |
| 5-1 | 13 | 0.022 | Intermediate |
| 5-1 | 14 | 0.007 | Intermediate |
| 7-4 | 5 | 0.071 | Tolerant |
| 7-4 | 6 | 0.089 | Tolerant |
| 13-17 | 7 | 0.014 | Intermediate |
| 21-1 | 5 | 0.348 | Sensitive |
| 21-1 | 6 | 0.082 | Sensitive |
| 21-1 | 7 | 0.077 | Sensitive |
| 21-1 | 8 | 0.068 | Sensitive |
| 21-1 | 9 | 0.992 | Sensitive |
| 21-1 | 11 | 0.091 | Sensitive |
| 21-1 | 12 | 0.284 | Sensitive |

TABLE 29-continued

Herbicide resistance assays of transgenic strawberry lines

| Line number | Plant number | CP4 level (ppm) | Phentype |
|---|---|---|---|
| 82-2 | 13 | 0.165 | Tolerant |
| 82-2 | 15 | 0.141 | Tolerant |

Example 12
Strawberry NPTII ELISA Assays

An NPTII ELISA assay was completed for a number of independent lines from several different constructs. The results shown below demonstrate that NPTII selection works efficiently for the disclosed strawberry transformation methods and does not appear to be dependent on the plasmid construct used. Plasmid pMON1 8349 (pGSRE2-AGO-Nos3') contains the Aspergillus glucose oxidase gene, plasmid pMON18324 (pFMV-SRE49F-Nos3') contains a strawberry ripening gene, and-plasmid pMON15737 (pFMV-CP4-E9 3') contains 5-enolpyruvylshikimate-3-phosphate synthase gene from Agrobacterium sp. strain CP4.

TABLE 30

NPTII ELISA data

| Construct | Conferred trait | # Lines tested | # Positive lines | # Negative lines |
|---|---|---|---|---|
| pMON18349 | Disease resistance | 16 | 13 | 1 |
| pMON18324 | Improved shelf life | 18 | 17 | 0 |
| pMON15737 | Herbicide tolerance | 5 | 4 | 1 |

Example 13
Progeny Data

Seeds from transgenic Pajaro strawberry plants containing plasmid pMON15737 were used to generate $R_1$ progeny plants. Shoots from the progeny were assayed with X-Gluc staining solution. These results indicate that exogenous nucleic acids may be transferred to progeny. As strawberry is octoploid, progeny often do not display simple Mendelian distributions.

TABLE 31

| Line | Total shoots | Number GUS positive |
|---|---|---|
| Pajaro 13-3 | 14 | 12 |
| Pajaro 6-9 | 29 | 1 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A method of preparing transgenic strawberry shoots, the method comprising:
   (a) contacting strawberry explants with *Agrobacterium tumefaciens* in a co-cultivation medium prepared using glucose or fructose, thereby producing transformed strawberry explants; and
   (b) culturing the transformed strawberry explants in a selection medium prepared using glucose or fructose, thereby producing transformed strawberry shoots.

2. The method of claim 1, further comprising culturing the transformed strawberry shoots in rooting medium prepared using glucose or fructose, thereby producing transgenic strawberry plants.

3. The method of claim 1, further comprising incubating the transformed strawberry explants for a delay period in delay media under low light conditions between about 0 $\mu$Einsteins m$^{-2}$ sec$^{-1}$ and about 40 $\mu$Einsteins m$^{-2}$ sec$^{-1}$.

4. The method of claim 3, wherein the low light conditions are between about 0 $\mu$Einsteins m$^{-2}$ sec$^{-1}$ and about 20 $\mu$Einsteins m$^{-2}$ sec$^{-1}$.

5. The method of claim 3, wherein the delay period is about 0 to about 5 days.

6. The method of claim 3, wherein the delay period is about 1 to about 4 days.

7. The method of claim 6, wherein the delay period is about 3 days.

8. The method of claim 3, wherein the delay medium contains glucose.

9. The method of claim 1, wherein the explants are prepared from micropropagated strawberry cultures.

10. The method of claim 1, wherein the explants are prepared from strawberry sheath leaves.

11. The method of claim 10, wherein the strawberry sheath leaves are runner leaves.

12. The method of claim 10, wherein the strawberry sheath leaves are node leaves.

13. The method of claim 10, wherein the strawberry sheath leaves are crown leaves.

14. The method of claim 10, wherein the strawberry sheath leaves are folded leaves.

15. The method of claim 1, wherein the co-cultivation medium, or the selection medium is prepared using glucose.

16. The method of claim 15, wherein the concentration of glucose is about 0.1% (w/v) to about 20% (w/v).

17. The method of claim 16, wherein the concentration of glucose is about 1% (w/v) to about 4% (w/v).

18. The method of claim 17, wherein the concentration of glucose is about 2% (w/v) to about 3% (w/v).

19. The method of claim 1, wherein the co-cultivation medium or the selection medium contains thidiazuron.

20. The method of claim 1, wherein the selection medium contains an auxin, a cytokinin, an antibiotic, or a plant selection agent.

\* \* \* \* \*

UNITED STATES PATENT AND TRADEMARK OFFICE
CERTIFICATE OF CORRECTION

PATENT NO.    : 6,274,791 B1
DATED         : August 14, 2001
INVENTOR(S)   : Seema Dhir, Maud A.W. Hinchee, Jeanne G. Layton and Janetta V. Oakes It is certified that error appears in the above-identified patent and that said Letters Patent is hereby corrected as shown below:

Title page,
Assignee, should read -- VPP Corporation --, and -- DNA Plant Technology Corporation --.

Signed and Sealed this

Fourteenth Day of May, 2002

Attest:

JAMES E. ROGAN
Attesting Officer
Director of the United States Patent and Trademark Office